United States Patent [19]

Rohr et al.

[11] 4,417,918
[45] Nov. 29, 1983

[54] HERBICIDAL α-[3-(2-HALO-4-TRIFLUOROMETHYL-PHENOXY)-6-HALOPHENOXY]PROPIONIC ACID THIO ESTERS AND ACIDS

[75] Inventors: Otto Rohr, Therwil, Switzerland; Georg Pissiotas, Lörrach, Fed. Rep. of Germany; Beat Böhner, Binningen; Kurt Burdeska, Basel, both of Switzerland

[73] Assignee: Ciba-Geigy Corporation, Ardsley, N.Y.

[21] Appl. No.: 297,299

[22] Filed: Aug. 28, 1981

Related U.S. Application Data

[60] Division of Ser. No. 83,905, Oct. 11, 1979, Pat. No. 4,304,926, which is a continuation-in-part of Ser. No. 883,021, Mar. 3, 1978, abandoned.

[30] Foreign Application Priority Data

Mar. 8, 1977 [CH] Switzerland ......................... 2867/77
Jul. 4, 1977 [CH] Switzerland ......................... 8182/77

[51] Int. Cl.³ ................. A01N 37/10; C07C 153/023; C07C 149/40; C07C 149/43
[52] U.S. Cl. ................. 71/100; 260/455 R; 562/426; 562/427
[58] Field of Search ...................... 260/455 R; 71/100; 562/426, 427

[56] References Cited

PUBLICATIONS

Noller, Textbook of Organic Chemistry, 2nd Edition, 1958, W. B. Saunders Co., p. 128.

*Primary Examiner*—Henry R. Jiles
*Assistant Examiner*—Robert C. Whittenbaugh
*Attorney, Agent, or Firm*—Frederick H. Rabin; Bruce M. Collins

[57] ABSTRACT

3-Phenoxy-α-phenoxy-alkancarboxylic acid derivatives of the formula

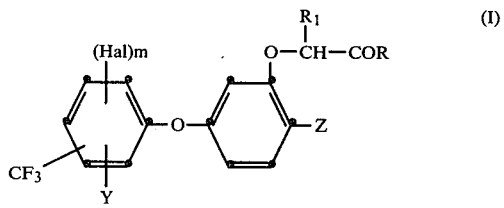

are disclosed as possessing a surprising selective herbicidal activity. In the formula Hal is a halogen atom, m is an integer 1, 2, or 3, Y is a hydrogen or halogen atom or the cyano group, Z is a halogen atom or the cyano group, $R_1$ is hydrogen or $C_1$–$C_8$ alkyl, and R is an acid function. Methods are disclosed for combatting weeds in mono- and dicotyledonous cultures such as cereals, corn, rice, soya and cotton, which comprise applying to the locus to be protected from weeds a dosage of from 0.1 to 10.0 kilograms per hectare of the above compounds.

8 Claims, No Drawings

HERBICIDAL α-[3-(2-HALO-4-TRIFLUOROMETHYLPHENOXY)-6-HALOPHENOXY]PROPIONIC ACID THIO ESTERS AND ACIDS

This is a division of application Ser. No. 083,905 filed on Oct. 11, 1979 now U.S. Pat. No. 4,304,926, which is a continuation-in-part of application Ser. No. 883,021 filed on Mar. 3, 1978 now abandoned.

DETAILED DISCLOSURE

The present application relates to a group of novel, herbicidally active substituent 3-phenoxy-α-phenoxy alkanecarboxylic acid derivatives which have a substituent in the α-phenoxy radical in the para-position to the 3-phenoxy-moiety, processes for their eir production, herbicidal compositions which contain these novel compounds as active ingredient, and to a method of selectively controlling weeds in crops of cultivated plants which comprises the use of these active ingredients or of compositions containing them.

The novel active compounds have the formula I

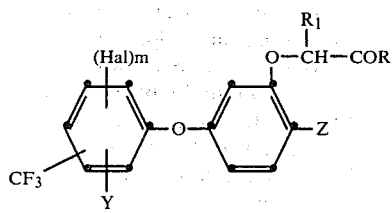

wherein

R is a radical ON=C($R_2$)$_2$, O$R_3$, S$R_4$ or N$R_5R_6$,

Hal is a halogen atom, m is an integer 0, 1 or 2,

Y is a hydrogen or halogen atom or the cyano group,

Z is a halogen atom or the cyano group, $R_1$ is hydrogen or $C_1$–$C_8$alkyl, $R_2$ are $C_1$–$C_4$alkyl or one $R_2$ is hydrogen, and $R_3$ is hydrogen or the cation of a base $(1/n)M^{n\oplus}$, in which M represents an alkali or alkaline earth metal cation or an iron, copper, zinc, manganese or nickel cation or an ammonio radical

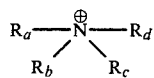

and n as an integer 1, 2 or 3 corresponds to the valency of the cation, while $R_a$, $R_b$, $R_c$ and $R_d$, each independently of the other, represent hydrogen, benzyl or a $C_1$–$C_4$alkyl radical which is unsubstituted or substituted by OH, NH$_2$ or $C_1$–$C_4$alkoxy; $R_3$ and $R_4$ are also hydrogen, $C_1$–$C_8$alkyl unsubstituted or substituted by halogen, cyano, $C_1$–$C_4$alkoxy, $C_1$–$C_4$alkylthio, $C_2$–$C_8$alkanoyl, $C_2$–$C_8$alkoxycarbonyl, bis($C_1$–$C_4$alkyl)amino, $C_3$–$C_8$cycloalkyl or cycloalkenyl, and also by a phenyl or phenoxy radical which is unsubstituted or mono- to trisubstituted by halogen, $C_1$–$C_4$alkyl or $C_1$–$C_4$alkoxy; or by a 5–6 membered heterocyclic radical;

a $C_3$–$C_8$alkenyl or alkynyl radical which is unsubstituted or mono- to tetrasubstituted by halogen, a $C_3$–$C_{12}$cycloalkyl or cycloalkenyl radical which is unsubstituted or substituted by halogen, a phenyl radical which is unsubstituted or mono- to trisubstituted by halogen, $C_1$–$C_4$alkyl, $C_1$–$C_4$alkoxy, $C_1$–$C_4$alkylthio, nitro, cyano or trifluoromethyl;

$R_5$ and $R_6$ represent hydrogen, $C_1$–$C_6$alkyl, which may be interrupted by oxygen or sulfur or an imino group or substituted by halogen, cyano or hydroxyl;

$C_2$–$C_6$alkenyl or alkynyl, optionally substituted by halogen; $C_3$–$C_8$ cycloalkyl or cycloalkenyl or $R_5$ and $R_6$ together with the nitrogen atom, to which they are attached can also form a heterocyclic ring system with 5 to 6 ring members, with the proviso that in the meaning of R, $R_3$ cannot be hydrogen, a metal cation or $C_1$–$C_8$alkyl unsubstituted or substituted by $C_1$–$C_4$alkyl when Z is halogen and the radical CF$_3$ is in a para-position and Y and/or (Hal)n are halogen atoms in the ortho-position to the oxygen bridge between the phenyl rings.

In the above formula, the alkyl radicals are both branched and unbranched and contain the indicated number of carbon atoms. The substituents $R_5$ and $R_6$ are preferably hydrogen or $C_1$–$C_4$ alkyl radicals. However, individual alkyl radicals can also be cyclic, preferably cyclopropyl or cyclohexyl, aromatic, e.g. a phenyl radical, araliphatic, like benzyl, or the two radicals together with the nitrogen atom to which they are attached can also form a heterocyclic ring system which contains 5 to 6 ring members.

Similar phenoxy-phenoxy-alkanecarboxylic acid derivatives which, however, carry the alkanecarboxylic acid radical in the paraposition, are known from German Offenlegungsschriften Nos. 2,136,828, 2,223,894, 2,433,067 and 2,531,643.

These known compounds have a special action against grasses and are suitable for the selective control of grass-like weeds in crops of mono- and dicotyledonous plants. However, they have no action at all against dicotyledonous weeds, or are only effective if used in very high rates of application.

The surprising discovery has now been made that the novel phenoxy-α-alkanecarboxylic acid derivatives of the formula I, which have the alkanecarboxylic acid radical in the meta-position, are highly suitable for controlling dicotyledonous weeds in crops of primarily monocotyledonous plants, such as cereals (e.g. wheat, barley, sorghum), maize, and also for controlling Sagittaria and Cyperus species in rice, as well as individually for selectively controlling weeds in crops of dicotyledonous plants, such as sugar beat, soya, and cotton.

A particularly good tolerance to rice—both hill rice and transplanted lowland rice—has been observed.

The compounds of the formula I are most effective against the following dicotyledonous weeds: *Sagittaria pygmea, Sinapis alba, Sida spinosa, Sesbania exaltata, Ipomoea purpurea, Galium aparine, Chrysanthemum leucum, Abutilon, Solanum nigrum, Ammania indica, Rotala indica, Cyperus difformis, Elatine triandra, Lindernia procumbens* etc.

Although the novel compounds also have a good preemergent action, their postemergent action is especially effective and advantageous.

A number of the novel active compounds are also suitable for desiccation and defoliation in cotton and potato crops shortly before harvesting.

The rates of application of herbicide of the present invention per hectare vary, depending on the activity of the respective active substance, the nature of the soil, climatic and weather conditions, the nature and time of application and the type of crop and the weeds to be controlled, between 0.1 and 10 kg, preferably between 0.5 and 4 kg.

Particularly suitable compounds are those of the formulae

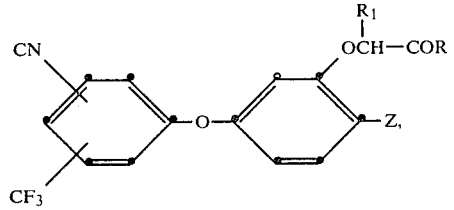
(Ia)

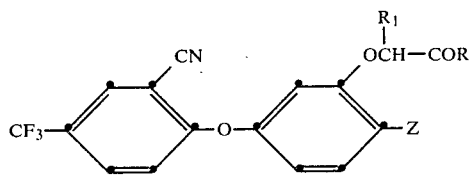
(Ib)

wherein R, $R_1$ and Z have the above-given meaning, further the 3-(2'-cyano-4'-trifluoromethylphenoxy)-α-(6-chlorophenoxy)-propionic acid-methyl and allyl esters, as well as the ones of the formula Ic

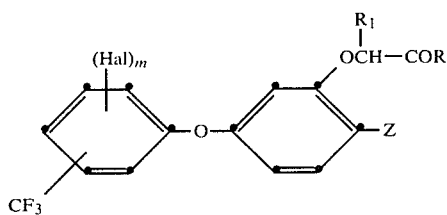
(Ic)

wherein Hal, m, R, $R_1$ and Z have the meaning given under formula I, with the proviso that in the meaning of R, $R_3$ cannot be hydrogen, a metal cation or $C_1$-$C_8$ alkyl unsubstituted or substituted by $C_1$-$C_4$ alkoxy when Z is halogen and the radical $CF_3$ is in the para-position and one or two halogen atoms occupy the ortho-position to the oxygen bridge between the phenyl rings.

Within this group of compounds were particularly interesting those of the formula Id

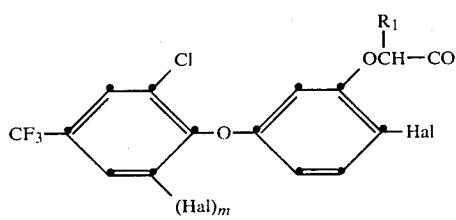
(Id)

wherein Hal, m, R and $R_1$ have the above-given meaning with the proviso that within the meaning of R, $R_3$ cannot be hydrogen, a metal cation or $C_1$-$C_8$ alkyl unsubstituted or substituted by $C_1$-$C_4$alkoxy; of the formulae

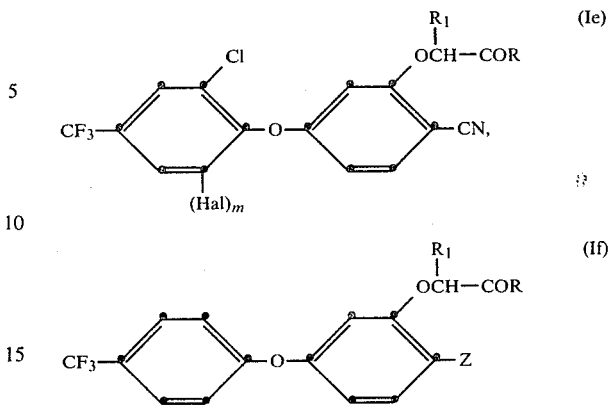
(Ie)

(If)

wherein Hal, m, R, $R_1$ and Z have the above-given meaning, further the compounds
3-(2'-chloro-4'-trifluoromethylphenoxy)-α-(6-chlorophenoxy)-propionic acid-acetoxim-ester,
3-(2'-chloro-4'-trifluoromethylphenoxy)-α-(6-chlorophenoxy)-propionic acid-methoxy-methyl amide,
3-(2'-chloro-4'-trifluoromethylphenoxy)-α-(6-chlorophenoxy)-propionic acid-benzyl ester,
3-(2'-chloro-4'-trifluoromethylphenoxy)-α-(6-chlorophenoxy)-propionic acid-benzylthio ester,
3-(2'-chloro-4'-trifluoromethylphenoxy)-α-(6-chlorophenoxy)-propionic acid-(2''-chloroethyl)ester,
3-(2'-chloro-4'-trifluoromethylphenoxy)-α-(6-chlorophenoxy)-propionic acid-(2''-cyanoethyl)ester,
3-(2'-chloro-4'-trifluoromethylphenoxy)-α-(6-chlorophenoxy)-propionic acid-cyclohexyl ester.

The novel compounds of the formula I are manufactured by the methods which are known per se for such syntheses.

The last step of the synthesis always consists of the following reaction step and constitutes the process of the present invention:

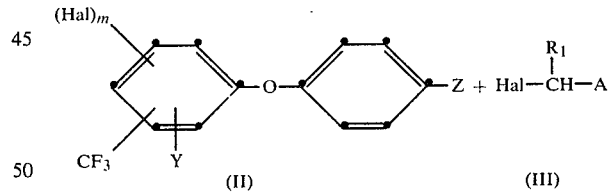
(II)         (III)

Accordingly, a start is made from a 3-hydroxy-diphenyl ether of the formula II, which is reacted with an α-halogen-alkanoic acid derivative or with a nitrile of the formula III in the presence of a base.

If a carboxylic acid (A≡COOH) is used as starting material of the formula III in this process, then this group can subsequently be converted into another derivative of the formula I as defined herein, either direct or by way of the corresponding acid chloride.

If an ester of the formula III is used, the ester group can be converted by saponification into the free carboxylic acid, a salt thereof, and then into an amide.

In the formulae II and III of the starting materials, n and the symbols A, X, Y and Z are as defined in formula I and Hal represents a halogen atom, such as chlorine, bromine etc.

The above reaction can be carried out in the presence or absence of solvents or diluents which are inert to the reactants. Polar organic solvents, such as methyl ethyl ketone, dimethyl formamide, dimethyl sulphoxide etc., are preferred. The reaction temperatures are between 0° and 200° C., preferably between 20° and 100° C., and the reaction time is from 1 hour by several days, depending on the starting material, choice of reaction temperature, and the solvent. The process is usually carried out under normal pressure. Suitable bases (condensation agents) for the reaction are those customarily employed, for example KOH, NaOCH$_3$, NaHCO$_3$, K$_2$CO$_3$, potassium tert-butylate etc., and also organic bases, such as triethylamine.

The starting materials of the formula III are known or they can be prepared by conventional methods. Many starting phenols of the formula III are also already known.

Phenoxyphenols of the formula II which have not yet been described can be easily prepared by conventional methods and techniques, for example as described in German Offenlegungsschriften Nos. 2,433,066 and 2,433,067.

Accordingly, for example, 2-methoxy-4-chloro-nitrobenzene of the formula

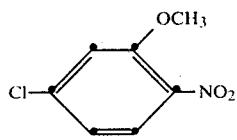

can be reacted with a phenol of the formula IV

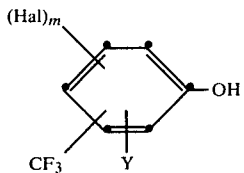

in an alkaline medium, to give the nitro compound of the formula V

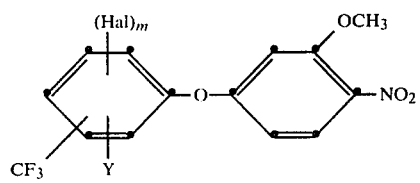

for example in accordance with the particulars of German Offenlegungsschrift No. 2,304,006.

The same nitro compound is also obtained by reaction of 2 moles of a phenol of the formula IV with 2,4-dichloronitrobenzene. In this reaction, a compound of the formula

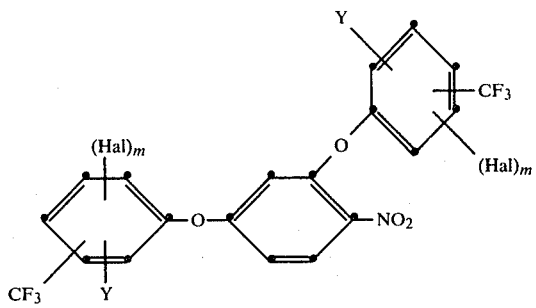

in formed as intermediate, which is then "transetherified" by heating with methanol and KOH in dioxane to give the methoxy compound V (method described in German Offenlegungsshcrift No. 2,533,172).

The resulting nitrated intermediate V is reacted by a conventional reduction of the nitro group to give the corresponding amine, which is then converted into the diazonium salt (e.g. diazonium chloride). Finally, the diazo group of the diazonium salt is replaced by conventional methods by the cyano group or by a halogen atom.

The reduction of the nitro group in V is carried out catalytically with hydrogen (for example with Raney nickel) in solution in an inert solvent, or by gradual addition of V to a mixture of iron powder and dilute hydrochloric acid at elevated temperature.

The diazotisation of the resulting amine is effected in conventional manner in solution in dilute hydrochloric acid by the dropwise addition of an aqueous NaNO$_2$ solution at temperatures below 5° C.

The substitution of the cyano group for the diazo group is carried out by the dropwise addition of the disodium salt to an aqueous solution of K$_3$[Cu(CN)$_4$] or by addition of copper powder and copper (I) cyanide to the solution of the diazonium salt. These reactions to give p-cyano-diphenyl-ethers, starting from substituted p-nitro-diphenyl ethers have already been described in German Offenlegungsschrift No. 1,912,600.

The substitution of chlorine for the diazo group is effected by addition of copper (I) chloride (CuCl) and finely divided copper powder to the diazonium chloride solution.

The substitution of bromide for the diazo group is best effected by addition of KBr and CuBr to a diazonium salt solution, whilst the substitution of iodine for the diazo group can be carried out by treating diazonium salt with potassium iodide.

The halogen atom represented by Z can also be obtained by halogenating the diphenyl ether which is unsubstituted in the 4'-position.

In order finally to obtain the corresponding free starting phenol of the formula II from the compounds prepared in the manner described above, the ether protective group in the meta-position (—O—CH$_3$) is cleaved, for example with HBr in glacial acetic acid.

The production of a number of phenoxy-phenoxyalkanecarboxylic acid derivatives of the formula I is illustrated in the following Examples. Further active compounds obtained in corresponding manner are listed in the subsequent table.

Temperatures are given in degrees Centigrade, parts and percentages are by weight; the pressures are given in Torricelli (torr) or mm Hg (=1.33 millibar).

EXAMPLE 1

3-(2'-cyano-4'-trifluoromethylphenoxy)-α-(6-chlorophenoxy)-propionic acid-methyl ester

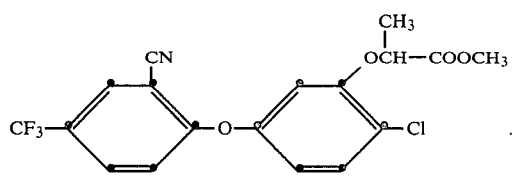

To a solution containing 15.9 g (0.05 Mol) of 3-(2'-cyano-4'-trifluoromethylphenoxy)-6-chlorophenol and 50 ml of 2-bromopropionic acid-methyl ester in 100 ml of methylethylketone is added 19.5 g potassium carbonate and 1 g potassium iodide. This mixture is heated to 100° in a water bath and stirred overnight. Then it is filtered, the filtrate is concentrated under reduced pressure and the remaining oil is distilled under high vacuum. The main fraction passes at 189°/0.01 torr as clear oil. Yield 15 g.

EXAMPLE 2

3-(2'-cyano-4'-trifluoromethylphenoxy)-α-(6-chlorophenoxy)-propionic acid

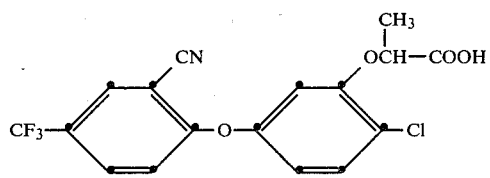

60 g (0.15 Mol) of the methyl ester obtained in Example 1 are dissolved in 400 ml of methanol and 100 ml of 2 n methanolic sodium hydroxide solution is added thereto. This reaction mixture is stirred for 3 hours at room temperature. The solvent is then evaporated under reduced pressure and the residue dissolved in water. After acidifying with concentrated hydrochloric acid, the acid separates as viscous oil. After extraction with a mixture of ethyl acetate and toluene 1:1, and evaporation of the solvent, there remains 61.5 g of the above acid as a clear viscous oil.

EXAMPLE 3

3-(2'-cyano-4'-trifluoromethylphenoxy)-α-(6-chlorophenoxy)-propionic acid-allyl ester

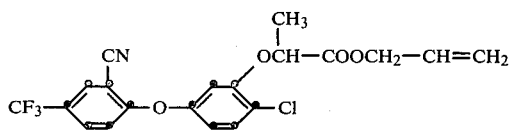

55 g (0.15 Mol) of the acid obtained in Example 2 are dissolved in 120 ml of toluene. Then 2 ml of pyridine and 40 ml of thionyl chloride are added thereto. This mixture is stirred for 3 hours at 80°. Then the solvents are distilled off under reduced pressure and the remaining oil (56 g) is dissolved in 200 ml of toluene. To this solution is added dropwise, at a temperature of 5°–15°, first 12.5 g of allyl alcohol, then 28 g of triethylamine. This reaction mixture is stirred overnight at room temperature and then added with 50 ml of water. The organic phase is separated, dried over sodium sulfate, filtered and then evaporated to dryness. The residue represents 57.8 g of a dark oil, which is dissolved in toluene and cleaned by chromatography over an alumina oxide column. After evaporation of the toluene and distillation, there remains 54 g of the allyl ester as a clear oil, b.p. 165°/0.01 torr.

analysis C: found 56.7%; C: calc. 56.42%; H: found 3.8%; H: calc. 3.55%; N: found 3.1%; N: calc. 3.29%.

In analogy to these Examples, the following compounds were prepared:

3-(3'-trifluoromethylphenoxy)-α-(6-chlorophenoxy)-propionic acid-methyl ester, b.p. 183°/0.01 torr Further the compounds listed in the table below:

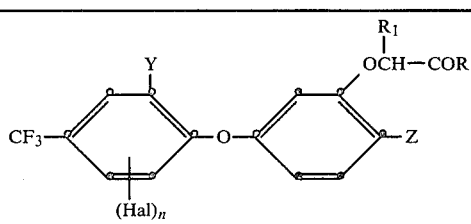

| Compound No. | Y | (Hal)$_n$ | Z | R$_1$ | R | physical data |
|---|---|---|---|---|---|---|
| 1 | Cl | — | Cl | CH$_3$ | OCH$_3$ | b.p. 179°(Known)/0.01 torr |
| 2 | H | — | Cl | CH$_3$ | OCH$_3$ | b.p. 165°/0.01 torr |
| 3 | CN | — | Cl | CH$_3$ | OCH$_3$ | m.p. 103–7° |
| 4 | H | — | Cl | CH$_3$ | OH | m.p. 110–120° |
| 5 | CN | 6-Cl | Cl | CH$_3$ | OCH$_2$—CH=CH$_2$ | b.p. 165°/0.01 torr |
| 6 | H | — | Cl | CH$_3$ | OCH$_2$—⌬ | b.p. 193°/0.03 torr |
| 7 | H | — | Cl | CH$_3$ | OC$_4$H$_9$sec | b.p. 173°/0.15 torr |
| 8 | H | 5-Cl | Cl | CH$_3$ | OCH$_3$ | b.p. 167/0.07 torr |
| 9 | Cl | — | Br | NCH$_3$ | OCH$_3$ | b.p. 165° (Known) |
| 10 | Cl | — | I | CH$_3$ | OCH$_3$ | b.p. 157–164°/0.03 (Known) |
| 11 | H | — | I | CH$_3$ | OCH$_3$ | b.p. 171°/0.35 torr |
| 12 | H | — | CN | CH$_3$ | OCH$_3$ | b.p. 176°/0.02 torr |

-continued

| | | | | | | |
|---|---|---|---|---|---|---|
| 13 | Cl | — | CN | CH$_3$ | OCH$_3$ | oil |
| 14 | Cl | — | Cl | CH$_3$ | ON=C(CH$_3$)$_2$ | n$_D^{24}$ 1.5293 |
| 15 | Cl | — | Cl | CH$_3$ | N(CH$_3$)OCH$_3$ | n$_D^{23}$ 1.5275 |
| 16 | Cl | — | Cl | CH$_3$ | 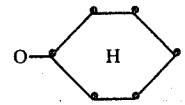 O—⟨ ⟩—H | m.p. 61–65° |
| 17 | H | — | CN | CH$_3$ | OC$_4$H$_9$n | oil |
| 18 | H | — | CN | CH$_3$ | OC$_4$H$_9$sec | oil |
| 19 | H | — | CN | CH$_3$ | 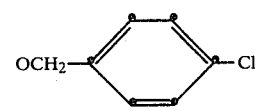 OCH$_2$—⟨ ⟩—Cl | oil |
| 20 | H | — | CN | CH$_3$ | ON=C(CH$_3$)$_2$ | |
| 21 | H | — | CN | CH$_3$ | N(C$_2$H$_5$)$_2$ | oil |
| 22 | H | — | CN | CH$_3$ | OC$_2$H$_4$N(C$_2$H$_5$)$_2$ | oil |
| 23 | Cl | — | Cl | CH$_3$ | 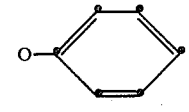 O—⟨ ⟩ | b.p. >200°/0.01 torr |
| 24 | Cl | — | Cl | CH$_3$ | OC$_2$H$_4$N(C$_2$H$_5$)$_2$ | m.p. 126–128° |
| 25 | Cl | — | Cl | CH$_3$ | 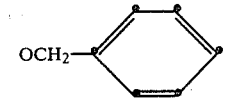 OCH$_2$—⟨ ⟩ | oil |
| 26 | Cl | — | Cl | CH$_3$ | 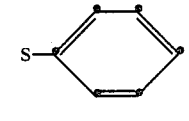 S—⟨ ⟩ | oil |
| 27 | Cl | — | Cl | CH$_3$ | OC$_2$H$_4$Cl | m.p. 61–62° |
| 28 | Cl | — | Cl | C$_8$H$_{17}$n | OC$_2$H$_5$ | viscous oil |
| 29 | Cl | — | Cl | CH$_3$ | OCH(CH$_3$)CN | n$_D^{24}$ 1.5215 |
| 30 | Cl | — | Cl | CH$_3$ | OCH$_2$CN | n$_D^{24}$ 1.5340 |
| 31 | Cl | — | Cl | CH$_3$ | OC$_2$H$_4$CN | n$_D^{24}$ 1.5295 |
| 32 | Cl | — | Cl | CH$_3$ | OCH$_2$COCH$_3$ | n$_D^{24}$ 1.5260 |
| 33 | Cl | — | Cl | CH$_3$ | OC$_2$H$_4$SCH$_3$ | n$_D^{24}$ 1.5375 |
| 34 | Cl | — | Cl | CH$_3$ | 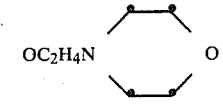 OC$_2$H$_4$N⟨ ⟩O | oil |
| 35 | Cl | — | Cl | CH$_3$ | 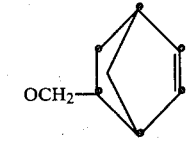 OCH$_2$—⟨ ⟩ | oil |
| 36 | Cl | — | Cl | CH$_3$ | NHC$_2$H$_4$OCH$_3$ | n$_D^{24}$ 1.5330 |
| 37 | Cl | — | Cl | CH$_3$ | 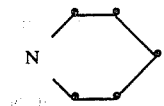 N⟨ ⟩ | oil |
| 38 | Cl | — | Cl | CH$_3$ | 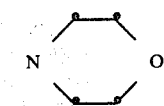 N⟨ ⟩O | oil |
| 39 | Cl | — | Cl | CH$_3$ | OCH$_2$CF$_3$ | n$_D^{24}$ 1.5015 |

| | | | | | -continued | |
|---|---|---|---|---|---|---|
| 40 | H | — | Br | CH₃ | OCH₃ | oil |
| 41 | CN | — | I | CH₃ | OCH₃ | oil |
| 42 | CN | — | CN | CH₃ | OCH₃ | oil |
| 43 | CN | — | Br | CH₃ | OCH₃ | oil |
| 44 | Cl | 6Br | Cl | CH₃ | OCH₃ | oil |
| 45 | Br | — | Cl | CH₃ | OCH₃ | oil |
| 46 | Cl | — | Cl | CH₃ | SH | |
| 47 | Cl | — | Br | CH₃ | SH | |
| 48 | Cl | — | Cl | CH₃ | S$^{\ominus}$$^{\oplus}$NH₂(C₂H₄OH)₂ | oil |

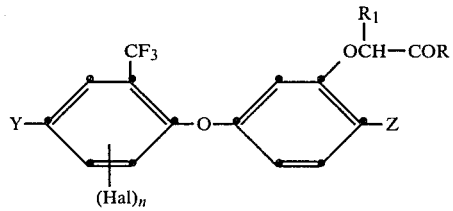

| Compound No. | Y | (Hal)$_n$ | Z | R₁ | R | physical data |
|---|---|---|---|---|---|---|
| 49 | H | 5-Cl | Cl | CH₃ | OCH₃ | b.p. 167°/0.07 torr |
| 50 | CN | — | Cl | CH₃ | OCH₃ | b.p. >200°/0.01 torr |
| 51 | Cl | — | Cl | CH₃ | OCH₃ | b.p. >200°/0.01 torr |
| 52 | Cl | — | CN | CH₃ | OCH₃ | b.p. >200°/0.01 torr |
| 53 | H | 3-Cl | Cl | CH₃ | OCH₃ | b.p. 174°/0.02 torr |

The novel active substances of the formula I are stable compounds which are soluble in conventional organic solvents, such as alcohols, ethers, ketones, dimethyl formamide, dimethyl sulphoxide etc.

The compositions of the present invention are obtained in known manner by intimately mixing and grinding active substances of the general formula I with suitable carriers and/or additives, with or without the addition of antifoam agents, wetting agents, dispersants and/or solvents which are inert to the active substances. The active substances can be processed to the following formulations:

solid formulations:

dusts, tracking powders, granules (coated granules, impregnated granules and homogeneous granules); active substance concentrates which are dispersible in water:

wettable powders, pastes, emulsions, emulsion concentrates; liquid formulations: solutions.

The concentrations of active substance in the compositions of this invention are between 1 and 80 percent by weight. As circumstances may require, the active substances can also be applied in low concentrations of about 0.05 to 1 percent by weight.

The compositions of the present invention can be mixed with other biocidal active substances or compositions. Thus in addition to containing the cited compounds of the formula I, the compositions of the present invention can also contain, for example, insecticides, fungicides, bactericides, fungistatic agents, bacteriostatic agents, nematocides or further herbicides, in order to broaden the activity spectrum.

Granules

The following substances are used to prepare 5% granules:

5 parts of one of the active substances of the formula I,
0.25 parts of epichlorohydrin,
0.25 parts of cetyl polyglycol ether,
3.50 parts of polyethylene glycol,
91 parts of kaolin (particle size 0.3–0.8 mm).

The active substance is mixed with epichlorohydrin and dissolved with 6 parts of acetone, and the polyethylene glycol and cetyl polyglycol ether are then added. The resultant solution is sprayed on kaolin and subsequently evaporated in vacuo.

Wettable Powder

The following constituents are used to prepare
(a) a 70% and (b) a 10% wettable powder:
(a)
70 parts of 3-(4'-trifluoromethyl-2'-chlorophenoxy)-α-(6-chlorophenoxy)-propionic acid methyl ester,
5 parts of sodium dibutylnaphthalene sulphate,
3 parts of naphthalenesulphonic acid/phenolsulphonic acid/formaldehyde condensate (3:2:1),
10 parts of kaolin,
12 parts of Champagne chalk;
(b)
10 parts of 3-(4'-trifluoromethylphenoxy)-α-(6-chlorophenoxy)-propionic acid methyl ester,
3 parts of a mixture of the sodium salts of saturated fatty alcohol sulphates,
5 parts of naphthalenesulphonic acid/formaldehyde condensate,
82 parts of kaolin.

The respective active substance is applied to the corresponding carriers (kaolin and chalk) and then these are mixed and ground, to yield wettable powders of excellent wettability and suspension powder. By diluting these wettable powders with water it is possible to obtain suspensions containing 0.1 to 80% of active substance. These suspensions are suitable for controlling weeds in cultivations of plants.

Paste

The following substances are used to prepare a 45% paste:
45 parts of 3-(4'-trifluoromethyl-2'-cyano-phenoxy)-α-(6-chlorophenoxy)-propionic acid methyl ester or one of the other cited active compounds of the formula I,
5 parts of sodium aluminium silicate, 14 parts of cetyl polyglycol ether with 8 moles of ethylene oxide,
1 parts of oleyl polyglycol ether with 5 moles of ethylene oxide,
2 parts of spindle oil,
10 parts of polyethylene glycol,
23 parts of water.

The active substance is intimately mixed with the additives in appropriate devices and ground. A paste is obtained from which, by dilution with water, it is possible to manufacture suspensions of the desired concentration of active substance.

Emulsifiable Concentrate

The following ingredients are mixed to prepare 25% emulsion concentrate:
  25 parts of 3-(2'-chloro-4'-trifluoromethylphenoxy)-α-(6-chlorophenoxy)-propionic acid benzyl ester
  5 parts of a mixture of nonylphenolpolyoxyethylene and calcium dodecylbenzenesulphonate,
  15 parts of cyclohexanone,
  55 parts of xylene.

This concentrate can be diluted with water to give emulsions in suitable concentrations of e.g. 0.1 to 10%. Such emulsions are suitable for controlling weeds in cultivations of plants.

The novel 3-phenoxy-α-phenoxyalkanecarboxylic acid derivatives of the formula I and the compositions which contain them have an excellent selective herbicidal action againt grass-like weeds in different crops of cultivated plants, and in addition they exert a plant growth regulating action.

A particularly preferred field of use is the selective control of chiefly, dicotyledonous weeds in cereal crops and, in addition, of Sagitaria and Cyperus species in rice. The dihalogenophenoxy-phenoxy-alkanecarboxylic acid derivatives, in particular dihalogenophenoxy-phenoxy-propionic acid derivatives, of the formula I, have proved to be most effective.

Although the novel active substances of the formula I are effective in pre- and post-emergent application, the post-emergent application as contact herbicide is preferred although the pre-emergent use is also of interest.

The novel active compounds of the formula I, formulated for example as 25% wettable powders or for example, as emulsifiable concentrates, and diluted with water, are preferably applied to the crops of plants in the post-emergent stage.

Herbicidal action on applying the active compounds after emergence of the plants (post-emergent application)

Different cultivated plants and grass-like weeds are reared from seeds in pots in a greenhouse until they have reached the 4- to 6-leaf stage. Then the plants are sprayed with aqueous active substance emulsions (obtained from a 20% emulsifiable concentrate) in different rates of application. The treated plants are then kept at optimum light, watering, temperature (22°-25° C.) and humidity (50-70% relative humidity) conditions. Evaluation of the test was made 15 days after treatment. The state of the plants is examined and rated.

In this test, almost all compounds tested severely damaged the dicotyledonous plants and weeds, whereas monocotyledonous cultures were largely unharmed and the grass-like weeds suffered only slight to medium-severe damage.

Selective herbicidal action on rice in the post-emergent procedure

Twenty-five-day-old rice plants are transplanted into large rectangular asbestos cement containers in a greenhouse. Seeds of the weeds occuring in rice crops, namely *Echinochloa crus* galli, *Sagittaria pygm., Cyperus difformis, Ammania indica, Rotala indica, Elantine trianda* and *Lindernia procumbens,* are then sown between the rows of rice plants. The containers are well watered and kept at a temperature of about 25° C. and at high humidity. Twelve days later, when the weeds have emerged and reached the 2-3 leaf stage, the soil in each of the containers is covered with a layer of water to a height of 2.5 cm. The active substance is then applied in the form of an emulsion concentrate with a pipette, or else in granule from, between the rows of plants. The emulsifiable concentrate is diluted and applied so that it corresponds to a field application rate of 4, 2, 1, and 0.5 kg respectively of active substance per hectare. The test is evaluated 4 weeks later. In this test, compounds 1 caused appreciable damage to the weeds *Ammania indica, Rotala indica, Lindernia, Elatine,* Cyperus and *Sagittaria. Echinochloa crus galli* was damaged merely slightly. The rice remained undamaged.

Desiccation and defoliation action

Cotton plants of the variety Deltapine were reared in earthenware pots in a greenhouse. After the first capsules had formed, the plants were sprayed with aqueous compositions of active substance 13 in a rate of application corresponding to 1, 2, 0.6 and 0.3 kg/ha respectively in field application. Untreated plants served as controls. The evaluation of the test was made 3, 7 and 14 days after application of the active substance by determining the degree of defoliation (percentage of fallen leaves) and of desiccation (drying out of the leaves remaining on the plant).

The results are reported in the Table below.

| Rate of application | Defoliation after | | | Desiccation after | | |
|---|---|---|---|---|---|---|
| | 3 days | 7 days | 14 days | 3 days | 7 days | 14 days |
| 1,2 kg/ha | 5% | 15% | 95% | 35% | 55% | 95% |
| 0,6 kg/ha | 5% | 50% | 95% | 35% | 35% | 95% |
| 0,3 kg/ha | 5% | 50% | 95% | 35% | 35% | 95% |

Only a few desiccated leaves remain on the plant. The other compounds that were tested showed similar results.

Selective herbicidal action on soya and cotton plants in the preemergent procedure A number of phenoxy-α-phenoxy-alkanecarboxylic acid derivatives of the formula I, especially those having a trifluoromethyl group in the molecule, act selectively on soya and cotton in preemergent application. The test plants are sown in pots containing sterilised garden soil in a greenhouse. The active substance is formulated to a 25% emulsifiable concentrate and applied in the form of an aqueous dispersion to the surface of the soil directly after sowing. The pots are sprayed with 100 ml of spray broth per m$^2$ and stood in the air-conditioned greenhouse at 22°-25° C. and 60 to 70% humidity, and watered every day. Control and evaluation of growth is made after 3 weeks and the state of the plants is evaluated in accordance with the rating previously referred to above. The compounds tested did not harm cotton or soya at a concentration of 1 kg/ha while all the weeds were damaged beyond recovery.

What we claim is:

1. A compound of the formula

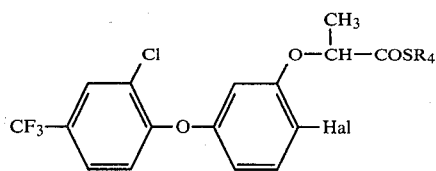

in which Hal is chlorine or bromine and $R_4$ is hydrogen, phenyl or benzyl.

2. 3(2'-Chloro-4-trifluormethylphenoxy)-α-(6-chlorophenoxy)-propionic-acid (2''-chloroethyl) ester, according to claim 1.

3. A herbicidal composition comprising (1) a herbicidally effective amount of a compound of the formula

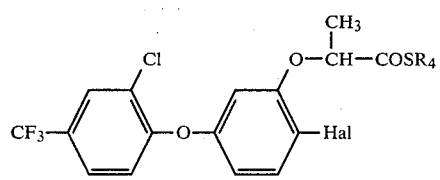

in which Hal is chlorine or bromine and $R_4$ is hydrogen or benzyl, and (2) a carrier.

4. A method of selectively controlling weeds in crops of cultivated plants which comprises applying areas where said crops are grown or to be grown, a herbicidally effective amount of a compound of the formula

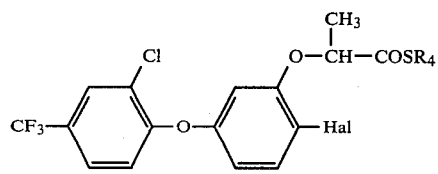

in which Hal is chlorine or bromine and $R_4$ is hydrogen or benzyl.

5. A method according to claim 8 in which the crops are treated in the post-emergence stage.

6. A method of desiccating and defoliating cultivated plants which comprises applying to said plants, before harvesting, an effective amount of a compound of the formula

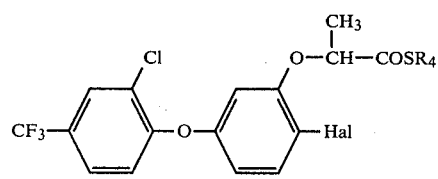

in which Hal is chlorine or bromine and $R_4$ is hydrogen or benzyl.

7. The phenylthioester of α-[3-(2-chloro-4-trifluoromethylphenoxy)-6-chlorophenoxy]propionic acid.

8. A method according to claim 4, wherein the crops are cereals, maize rice soya or cotton.

* * * * *